(12) United States Patent
Chang

(10) Patent No.: US 7,047,973 B2
(45) Date of Patent: May 23, 2006

(54) LARYNGEAL MASK AIRWAY

(76) Inventor: Ti-Li Chang, No. 35-1, Neydong Rd., Houli Hsiang, Taichung Hsien (TW)

( * ) Notice: Subject to any disclaimer, the term of this patent is extended or adjusted under 35 U.S.C. 154(b) by 0 days.

(21) Appl. No.: 10/961,117

(22) Filed: Oct. 12, 2004

(65) Prior Publication Data

US 2006/0076021 A1   Apr. 13, 2006

(51) Int. Cl.
*A61M 16/00* (2006.01)

(52) U.S. Cl. .............................. 128/207.15; 604/96.01

(58) Field of Classification Search .......... 128/200.26, 128/207.14, 207.15; 604/96.01
See application file for complete search history.

(56) References Cited

U.S. PATENT DOCUMENTS

| | | | | |
|---|---|---|---|---|
| 5,529,582 A | * | 6/1996 | Fukuhara | 606/205 |
| 5,881,726 A | * | 3/1999 | Neame | 128/207.15 |
| 5,983,897 A | * | 11/1999 | Pagan | 128/207.15 |
| 6,261,401 B1 | * | 7/2001 | Pagan | 156/182 |
| 6,668,821 B1 | * | 12/2003 | Christopher | 128/200.26 |
| 6,705,322 B1 | * | 3/2004 | Chang | 128/207.15 |
| 6,799,574 B1 | * | 10/2004 | Collins | 128/207.15 |
| 2004/0200479 A1 | * | 10/2004 | Chang | 128/207.14 |

FOREIGN PATENT DOCUMENTS

| GB | 2318735 | * | 5/1998 |
|---|---|---|---|
| GB | 2319478 | * | 5/1998 |
| GB | 2386325 | * | 9/2003 |

\* cited by examiner

*Primary Examiner*—Aaron J. Lewis
(74) *Attorney, Agent, or Firm*—Bacon & Thomas PLLC

(57) ABSTRACT

A laryngeal mask tube has of a dual-airway tube, a mask with an inflatable bladder and an inflation indicator device. The dual-airway tube has a primary tube communicated with the mask to guide gas into the body of a patient and a secondary tube communicated between with the bladder and the inflation indicator device. Two ribs are formed in the mask to prevent blockage of the primary tube and a tongue is formed inside the bladder to prevent the bladder from folding. Improvements of the laryngeal mask are that the tongue further has an easing hole to reduce rigidity of the tongue and the mask further has a fusing portion to integrally combine the dual-tube and the bladder together to avoid breakage at the bladder. Whereby, the laryngeal mask airway eliminates feelings of discomfort to patients and is durable in use.

2 Claims, 5 Drawing Sheets

LARYNGEAL MASK AIRWAY

BACKGROUND OF THE INVENTION

1. Field of the Invention

The present invention relates to a laryngeal mask airway for use with patients who are not able to breathe, and more particularly to a laryngeal mask airway that is convenient, comfortable and durable in use.

2. Description of Related Art

With reference to FIGS. 4 and 5, a conventional laryngeal mask airway in accordance with the prior art comprises a laryngeal mask (50), a dual-airway tube (55) and a laryngeal mask inflation indicator device (60).

The laryngeal mask (50) is teardrop-shaped to adapt to the larynx and is divided into a curved bottom face (not numbered) and a bladder (52) around the curved bottom face. An opening (not numbered) is defined in the curved bottom and at least one rib (62) longitudinally projects from curved bottom face near and below the opening. The bladder (52) having a pointed end and a rear obtuse end is made of soft material such as polyvinyl chloride (PVC). The bladder further has a tongue (54) extending forward from the pointed end of the bottom face inside the bladder (52) to prevent the bladder (52) refolding at the pointed end.

The dual-airway (55) communicates with the laryngeal mask (50) via the opening, has a connecting end and is composed of a primary tube (56) with an inner wall and a secondary tube (58) combined with the primary tube (56). The primary tube (56) is a large-bore tube made of resilient plastic material and communicates with the laryngeal mask (50) at the connecting end. The secondary tube (58) is formed inside walls of the primary tube (56) and has two ends. One end of the secondary tube (58) emerges from the primary tube (56) a distance from laryngeal mask (50) to connect to the inflation indicator device (60). The other end of the secondary tube (58) protrudes out from the primary tube (56) near the inflatable bladder (52) and directly communicates with the bladder (52).

However, the laryngeal mask airway still has the following drawbacks.

1. Although the tongue (54) can avoid the bladder (52) refolding at the pointed end, the tongue (54) also keeps a certain rigidity that may cause uncomfortable feeling when the tongue (54) abuts the larynx. Therefore, the laryngeal mask airway can not be smoothly placed into the patient's larynx.

2. With particular reference to FIG. 5, the laryngeal mask airway is easily broken at a joint between the secondary tube (58) and the bladder (52) when teeth inside the oral cavity block the bladder (58) and the laryngeal mask airway is improperly drawn out. Therefore, the laryngeal mask airway is not durable.

The present invention has arisen to mitigate and/or obviate the disadvantages of the conventional laryngeal mask airway.

SUMMARY OF THE INVENTION

The main objective of the present invention is to provide an improved laryngeal mask airway that is easily operated, and is comfortable and durable in use.

To achieve the foregoing objective, the laryngeal mask airway of the present invention comprises:

a dual-airway composed of a primary tube and a secondary tube combined with the primary tube, the secondary tube having a first end and a second end;

a mask adapted to cover the larynx and divided into a curved bottom face adjacent to the primary tube and an inflatable bladder with a pointed end around the curved bottom face that is connected to the first end of the secondary tube, the mask having:

an opening defined in the curved bottom face to communicate with the primary tube;

at least one rib longitudinally formed on the curved bottom face near the opening and adapted to prevent the epiglottis from covering the opening so gases can be transmitted into and out of the patient; and a tongue extending inside the bladder at the pointed end to prevent the bladder from refolding; and an inflation indicator device connecting to the second end of the secondary tube;

wherein the improvements of the laryngeal mask airway comprise:

the tongue has an easing hole defined in the tongue; and the mask further has a fusing portion formed between the bladder and the dual-airway and a through hole defined in the fusing portion to communicate the secondary tube to the bladder.

The easing hole on the tongue provides an easing efficiency to reduce rigidity of the tongue to ease the uncomfortable feeling when the laryngeal mask airway touches the larynx. Moreover, the fusing portion prevents the secondary tube from being exposed so as to eliminate breakage at joints between the secondary tube and the bladder.

Further benefits and advantages of the present invention will become apparent after a careful reading of the detailed description with appropriate reference to the accompanying drawings.

DETAILED DESCRIPTION OF THE INVENTION

Figure 1:
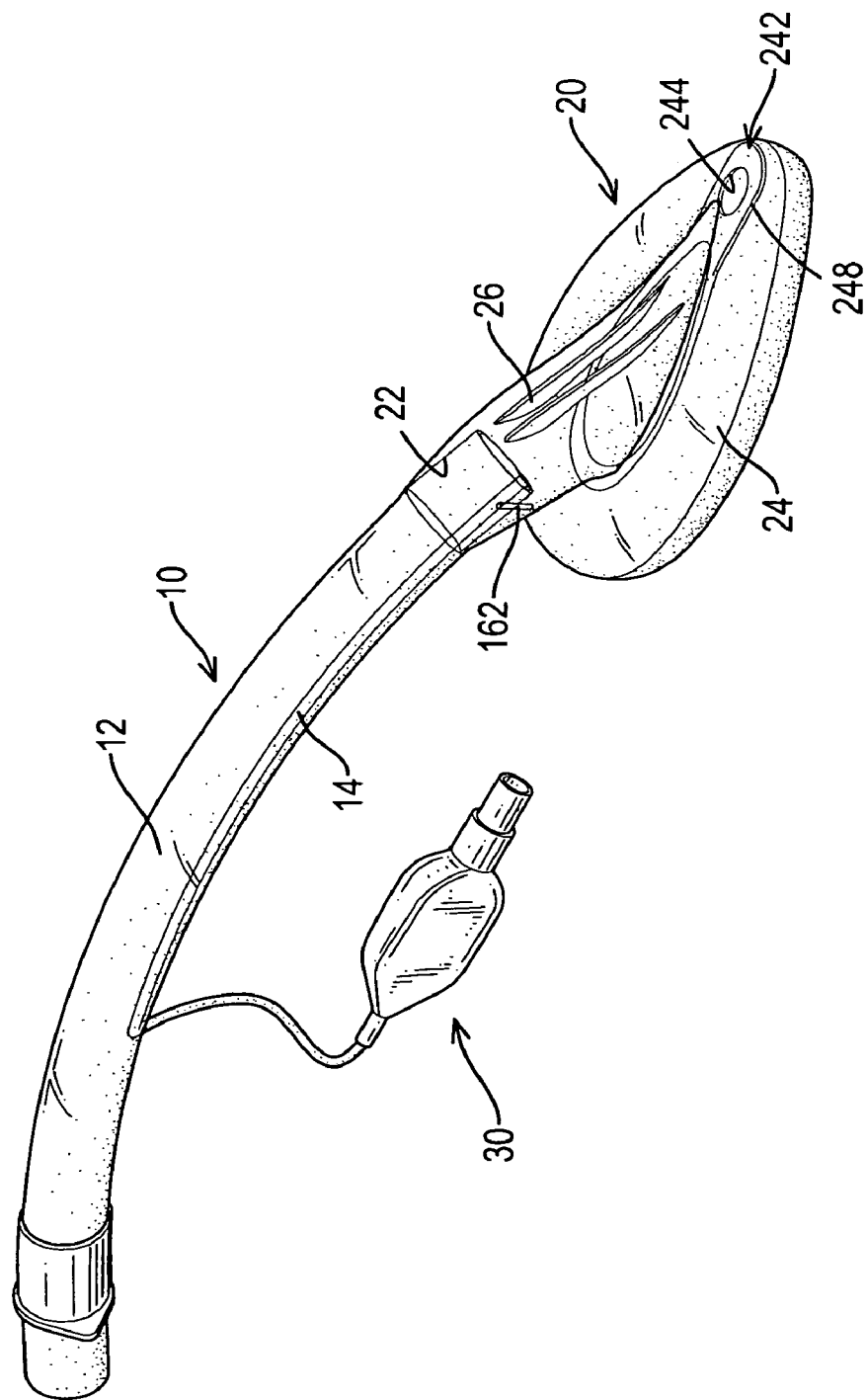
FIG. 1 is a perspective view of a laryngeal mask airway in accordance with the present invention.
Figure 2:
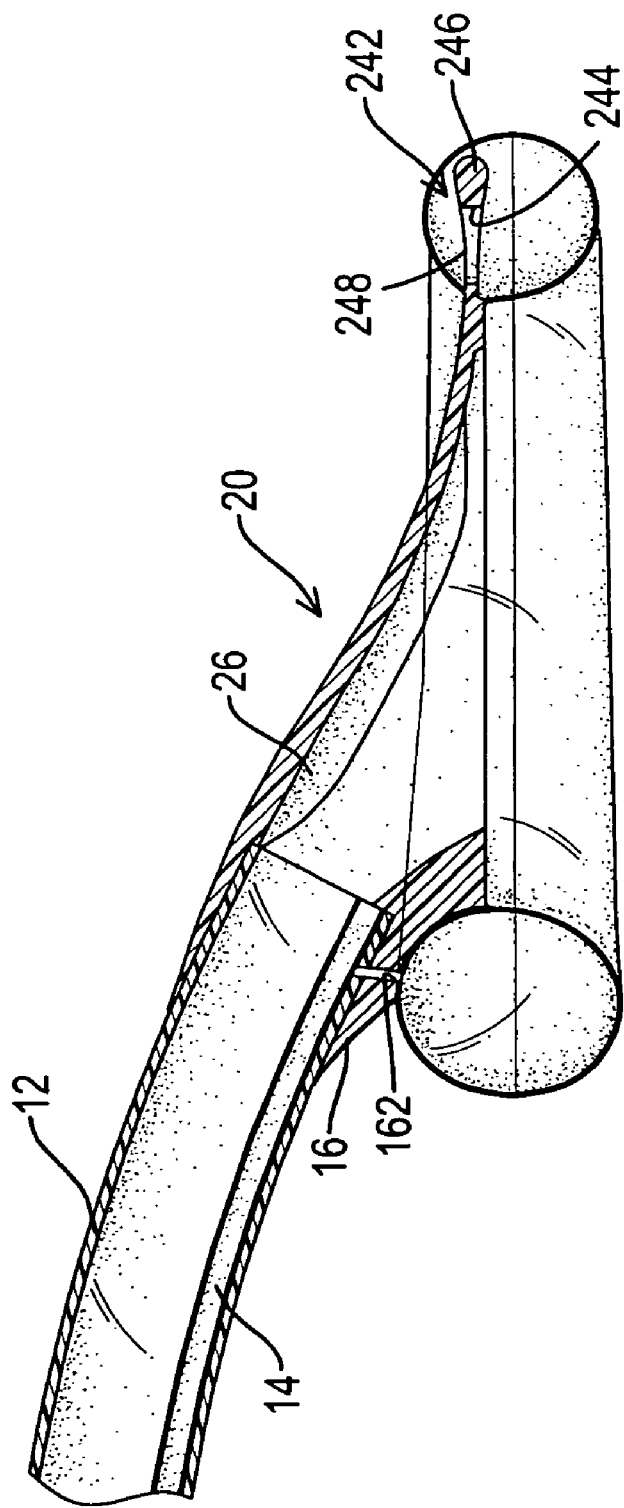
FIG. 2 is a cross-sectional side plan view of the laryngeal mask airway in FIG. 1.
Figure 3:
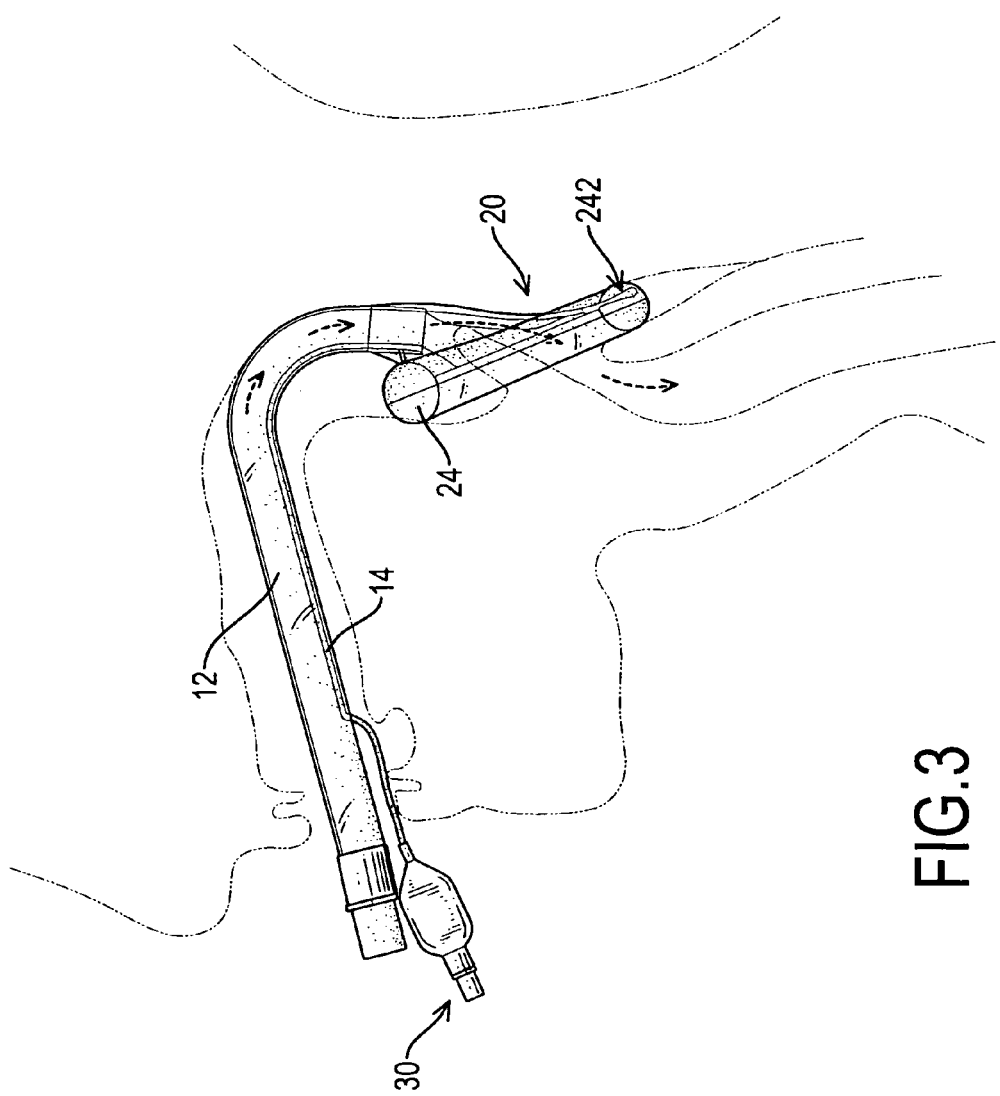
FIG. 3 is an operationally side plan view of the laryngeal mask airway inserted into the esophagus and over the larynx of a patient.
Figure 4:
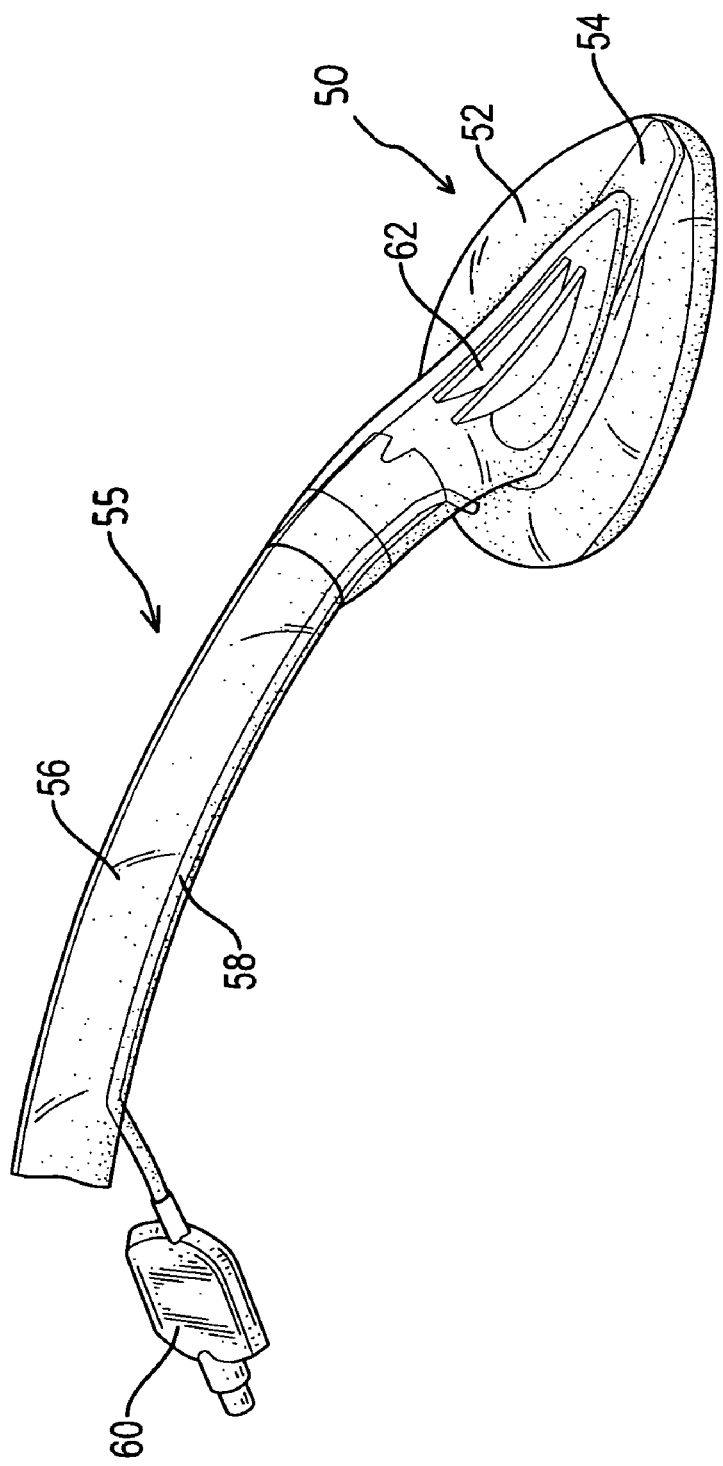
FIG. 4 is a perspective view of a conventional laryngeal mask.
Figure 5:
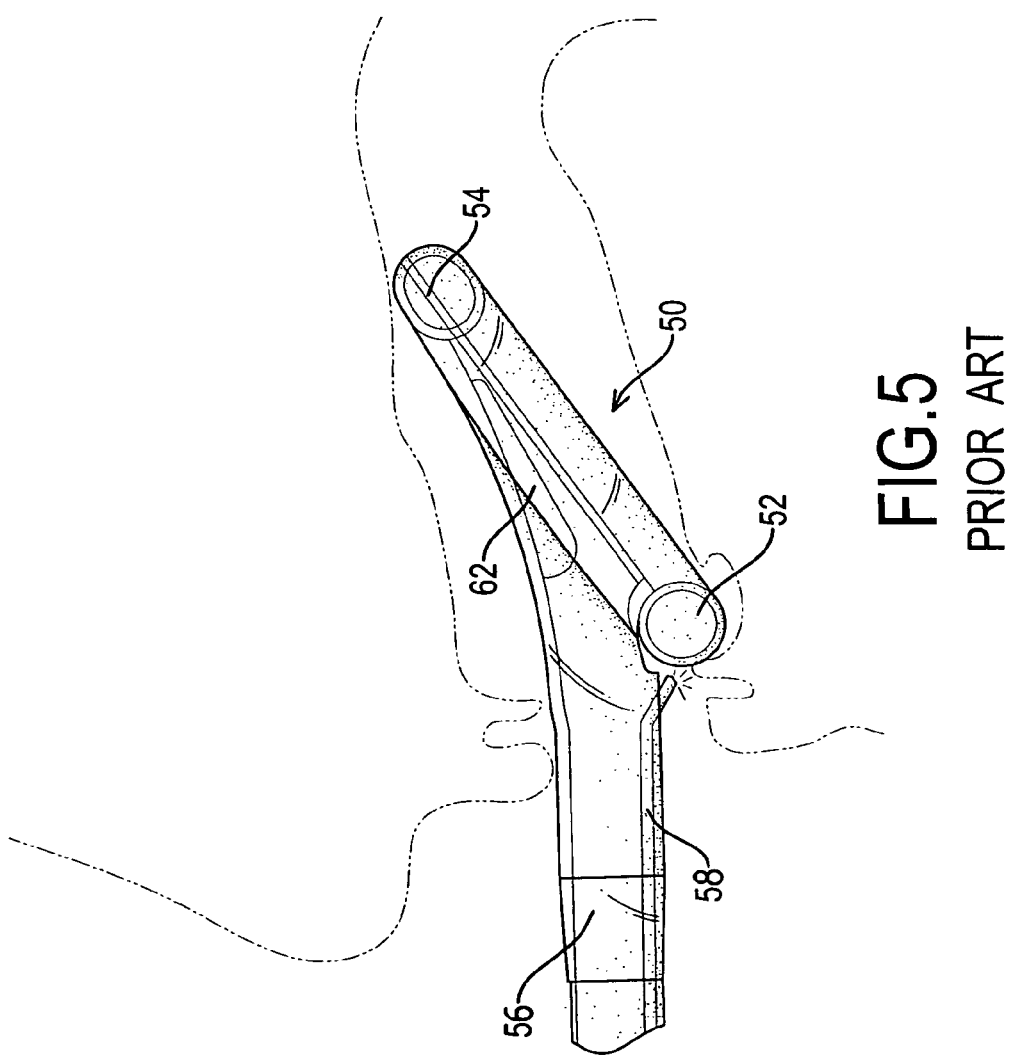
FIG. 5 is an operational side plan view of the conventional laryngeal mask airway inserted into the esophagus and over the larynx of a patient.

With reference to FIGS. 1, 2 and 3, a laryngeal mask airway in accordance with the present invention comprises a dual-airway tube (10), a laryngeal mask (20) and a laryngeal mask inflation indicator device (30).

The dual-airway (10) has a connecting end and is composed of a primary tube (12) with an inner wall and a secondary tube (14) combined with the primary tube (12). The primary tube (12) is a large-bore tube made of resilient plastic material and communicates with the laryngeal mask (20) at the connecting end. The secondary tube (14) is formed inside walls of the primary tube (12) and has two ends. One end of the secondary tube (14) emerges from the primary tube (12) a distance from laryngeal mask (20) to connect to the inflation indicator device (30). The other end of the secondary tube (14) extends toward to the laryngeal mask (20).

The laryngeal mask (20) is teardrop-shaped to adapt to the larynx and is divided into a curved bottom face (not numbered) adjacent to the primary tube (12) and a bladder (24) around the curved bottom face. An opening (22) is defined in the curved bottom face to communicate with the primary tube (12) and at least one rib (26) radially and longitudinally projects from the curved bottom face near the opening (22). The bladder (24), having a pointed end and a rear obtuse end, is made of soft material such as polyvinyl chloride (PVC) and has a tongue (242) extending forward from the pointed end of the bottom face inside the bladder (24). The secondary tube (14) is attached to, communicates with and inflates the bladder (24) by a syringe connected to the inflation indicator device (30) via the secondary tube (14).

The inflation indicator device (30) connected to the secondary tube (14) is conventional. To avoid unnecessary repetition of conventional knowledge and techniques, no further description of the inflation indicator device (30) is provided.

A first improvement of the laryngeal mask airway in the present invention is that the laryngeal mask (20) further has a fusing portion (16) extending between the bladder (24) and the dual-airway (10) and a through hole (162) defined in the fusing portion to communicate the secondary tube (14) to the bladder (24). The fusing portion (16) binds the bladder (24) and the dual-airway (10) together to allow the secondary tube (14) not to expose outside at the end near the laryngeal mask (20). Therefore, no joint is formed between the secondary tube (14) and the bladder (24) and the breakage of the bladder (24) is eliminated. The laryngeal mask airway in the present invention is durable.

A second improvement of the laryngeal mask airway in the present invention is that the tongue (242) has an easing hole (244) defined in the tongue (242) to reduce the rigidity of the tongue (242) and to make the tongue (242) bend easily. Moreover, the tongue (242) further has a round distal end (246) and a neck (248). The round distal end (246) obviates sharp abutment of the tongue (242) to make the patient comfortable when the laryngeal mask airway touches the larynx. The neck (248) provides more flexibility to the tongue (242) that also ease the rigidity of the tongue (242).

According to the foregoing description, the laryngeal mask airway of the present invention has the following advantages:

1. The tongue (242) has less rigidity whereby it can be elastically bent so that the laryngeal mask airway does not cause uncomfortable feeling to the patient.

2. The joint between the dual-airway (10) and the bladder (24) is not easily broken so that the laryngeal mask airway is durable.

Although the invention has been explained in relation to its preferred embodiment, it is to be understood that many other possible modifications and variations can be made without departing from the spirit and scope of the invention as hereinafter claimed.

What is claimed is:

1. A laryngeal mask airway adapted to be positioned over the larynx of a patient, and comprising:
   a dual-airway composed of a primary tube and a secondary tube combined with the primary tube, the secondary tube having a first end and a second end;
   a mask adapted to cover the larynx and divided into a curved bottom face adjacent to the primary tube and an inflatable bladder with a pointed end around the curved bottom face that is connected to the first end of the secondary tube, the mask having:
   an opening defined in the curved bottom face to communicate with the primary tube;
   at least one rib longitudinally formed on the curved bottom face near the opening and adapted to prevent the epiglottis from covering the opening so gases can be transmitted into and out of the patient; and
   a tongue extending inside the bladder at the pointed end to prevent the bladder from refolding;
   an inhalation indicator device connecting to the second end of the secondary tube;
   wherein the tongue has an easing hole defined in the tongue to reduce the rigidity of the tongue; and
   the mask further has a fusing portion formed between the bladder and the dual-airway and a through hole defined in the fusing portion to communicate the secondary rube to the bladder; and
   wherein the tongue further has a round distal end to lessen a patient's discomfort when in abutment with the mask.

2. The laryngeal mask airway as claimed in claim 1, wherein the tongue further has a round distal end and a neck.

* * * * *